United States Patent [19]

Kees

[11] Patent Number: 4,845,231
[45] Date of Patent: Jul. 4, 1989

[54] TETRAZOLES AND THEIR USE AS HYPOGLYCEMIC AGENTS

[75] Inventor: Kenneth L. Kees, West Chester, Pa.

[73] Assignee: American Home Products Corporation, New York, N.Y.

[21] Appl. No.: 155,386

[22] Filed: Feb. 12, 1988

[51] Int. Cl.$^4$ .................. C07D 257/02; C07D 213/62; C07D 403/06; C07D 411/12

[52] U.S. Cl. .................................... 548/252; 546/276; 548/253

[58] Field of Search ................ 548/252, 253; 514/381, 514/382, 340; 546/276

[56] References Cited

U.S. PATENT DOCUMENTS 3,435,115  3/1969  Holland ............................... 514/340
3,894,033  7/1975  Holland ............................... 548/250

FOREIGN PATENT DOCUMENTS 0046971  3/1982  Japan .................................. 548/253
595358  8/1974  Switzerland ......................... 548/253

OTHER PUBLICATIONS

Sohda et al.—Studies on Antidiabetic Agents. II. Synthesis of 5-[4-(1-methylcyclohexylmethoxy)benzyl]-thiazolidine-2,4-dione; 4/22/82.

Derwent Abstract 41767—Solidiuretic tetrazolyl-benzene:sulphonamide derivs.-prepd. e.g. by reaction of 4-thienyl-or furfuryl amino-2H-methyl—anilino-5-cyano benzene: sulfonamide with hydrazoic acid, 11/6/80.

Derwent Abstract 35639C/20 of J. 55047620—Pharmaceutical compsn. for treating gastric ulcers—contains opt. hydroxylated phenyl-alkylene, alkenylene, oxyalkylene or carboxy:alkylene carboxylic acid or tetrazole derivs.; 9/29/78.

Derwent Abstract 271464/44 of E.P. 123543—New alkanoic acid derivs.—useful as leukotriene antagonists for treating allergic and cardiovascular diseases; 4/21/83.

Primary Examiner—David B. Springer
Attorney, Agent, or Firm—Richard K. Jackson

[57] ABSTRACT

Compounds of the formula:

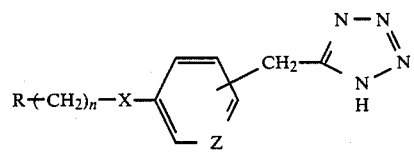

in which
R is a substituted or unsubstituted monocyclic or bicyclic alkyl group containing from 3 to 8 ring carbon atoms, wherein any substituent is alkyl of 1 to 3 carbon atoms, oxo, hydroxy, carboxy or when the hydroxy and carboxy substituents taken together they form a 1,3-carbonyloxy lactone ring closed structure;
n is one of the integers 0, 1, 2 or 3;
X is —O—,

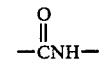

or —SO$_2$NH—; and
Z is =CH— or —N=;

or a pharmaceutically acceptable salt thereof, are antihyperglycemic agents.

8 Claims, No Drawings

TETRAZOLES AND THEIR USE AS HYPOGLYCEMIC AGENTS

BACKGROUND OF THE INVENTION

Ciglitazone (5-[4-(1-methylcyclohexylmethoxy)benzyl]-2,4-thiazolidinedione) has been shown by Sohda et al., Chem. Pharm. Bull. 30 (10) 3580–3600 (1982) to be a very potent hypoglycemic agent.

U.S. Pat. No. 3,894,033 discloses 5-aryltetrazoles, more specifically 5-(2-substituted-5-sulfamoylphenyl)-tetrazoles, as hypolipemic agents.

DESCRIPTION OF THE INVENTION

In accordance with this invention, there is provided a group of novel, substituted tetrazoles which are useful in lowering blood glucose levels in patients suffering from hyperglycemia. The anti-hyperglycemic agents of this invention present the following structural formula:

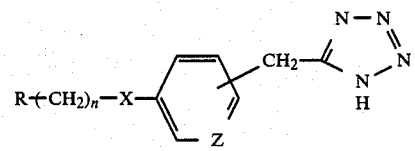

in which
R is a substituted or unsubstituted monocyclic or bicyclic alkyl group containing from 3 to 8 ring carbon atoms, wherein any substituent is alkyl of 1 to 3 carbon atoms, oxo, hydroxy, carboxy or a hydroxy and a carboxy substituent taken together to form a 1,3-carbonyloxy lactone closed ring structure;
n is one of the integers 0, 1, 2 or 3;
X is —O— or,

or —SO$_2$NH—; and
Z is =CH— or —N=;
or a pharmaceutically acceptable salt thereof.

Among these compounds, the preferred group of hypoglycemic agents are of the formula:

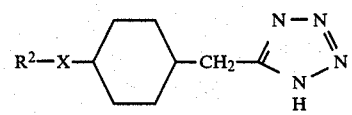

in which
R$^2$ is

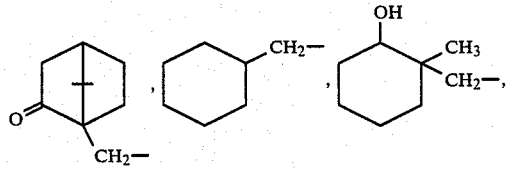

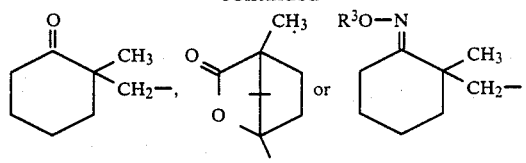

where
R$^3$ is hydrogen, alkyl of 1 to 6 carbon atoms, or benzyl;
X is —O—, X is —O—

or —SO$_2$NH—; or —SO$_2$NH—;
or a pharmaceutically acceptable salt thereof.

The pharmaceutically acceptable salts of the compounds of this invention include the alkali metal and amine salts of the 1H (or 2H) tetrazoles, such as the sodium, potassium, lower alkylamine, di(lower alkyl)amine, tri(lower alkyl)amine and the corresponding omega-hydroxy analogues (e.g. methylamine, ethylamine, propylamine, dimethylamine, diethylamine, dipropylamine, trimethylamine, triethylamine, tripropylamine, di(hydroxyethyl)amine, and the like.

It is to be understood that the tetrazolyl moiety, depicted throughout this application as 1H-tetrazol-5-yl, is capable of tautomerization to the 2H-tetrazol-5-yl moiety, thusly:

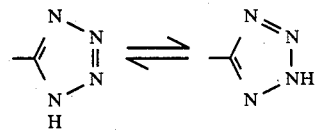

Hence, throughout this specification and claims, reference to the 1H tautomer is intended to also embrace the 2H tautomer.

The compounds of this invention are prepared by conventional methods well within the skill of the medicinal chemist. For example, acylation of 4-aminobenzylcyanide with the desired sulfonyl halide or carbonyl halide followed by reaction of the resulting nitrile with an alkali metal azide, affords the claimed compounds. Alkylation of hydroxyphenylacetonitrile with the appropriately sustituted cycloalkylmethylbromide or chloride followed by reaction of the resulting nitrile with an alkali metal azide afords the claimed ethers. Similarly, dehydration of the appropriately substituted hydroxymethylcyclohexane in the presence of hydroxyphenylacetonitrile with diethylazodicarboxylate triphenylphosphine adduct affords the desired ethers.

The following examples illustrate the production of representative compounds of the invention.

EXAMPLE 1

(+)-(7,7-Dimethyl-2-oxo-N-[4-(1H-tetrazol-5-ylmethyl)phenyl]bicyclo[2.2.1]heptane)-1-methanesulfonamide A mixture of 4-aminobenzylcyanide (9.28 g), triethylamine (14.3 g) and dichloromethane (200 mL) was cooled in an ice bath under a nitrogen atmosphere. To this mixture was added a solution of (+)-10-camphorsulfonylchloride (18.02 g) in dichloromethane (50 mL). The reaction was allowed to warm gradually to room temperature with stirring overnight. The reaction mixture was then poured onto 1N HCl solution in a separatory funnel and extracted twice with 1N HCl. The organic phase was then washed with saturated aqueous sodium chloride and dried over MgSO$_4$. After filtration and concentration with a rotary evaporator, the crude product was dissolved in a minimum amount of warm dichloromethane and diethyl ether was added. Storage at 0° C. produced 13.4 g of (+)-(7,7-dimethyl-2-oxo-N-[4-(cyanomethyl)phenyl]bicyclo[2.2.1]heptane)-1-methane sulfonamide as a tan solid, m.p. 162°–163° C. A second crop was crystallized from the mother liquor (5.4 g), m.p. 162°–184° C. A small sample was recrystallized from a hexane–ethyl acetate mixture. The white crystals obtained melt at 184°–186° C., $[\alpha]_D^{25} = +26.66$ (C. 0.075, 95% ethanol). However, the initial crop was of suitable purity to carry on to the next step.

A mixture of (+)-(7,7-dimethyl-2-oxo-N-[4-(cyanomethyl)phenyl]bicyclo[2.2.1]heptane)-1-methane sulfonamide (6.7 g, prepared in the preceding paragraph), sodium azide (6.3 g), ammonium chloride (5.2 g.) and dimethyl formamide (150 mL) was heated in an oil bath maintained at 124°–134° C. for 16 hours. The reaction was then cooled to room temperature and enough water was added to dissolve all of the solids. This mixture was then extracted with several portions of ethyl acetate. The extracts were washed with saturated aqueous sodium chloride solution and dired over MgSO$_4$. After filtration and concentration (high vacuum rotary evaporator, bath temperature 80° C.), the crude product was crystallized from acetone/diethyl ether to yield the title compound; m.p. 195°–196° C. (dec.); $[\alpha]_D = +22.7$ (C. 0.71, ethanol).

Elemental Analysis for C$_{18}$H$_{23}$N$_5$O$_3$S: Calc'd: C, 55.51; H, 5.95; N, 17.98; Found: C, 55.57; H, 5.97; N, 17.62.

A mixture of (+)-(7,7-dimethyl-2-oxo-N-[4-(1H-tetrazol-5-ylmethyl)phenyl]bicyclo[2.2.1]heptane)-1-methane sulfonamide (1.91 g, prepared in the preceding paragraph), potassium hydroxide (0.25 g.) and absolute ethanol (30 mL) was stirred under nitrogen at room temperature overnight. The solvent was removed in vacuo and the residue triturated with ethyl acetate. The white solid was dried under vacuum overnight to give 1.8 g of the title compound as the potassium salt; m.p. 274° C. (dec.); $[\alpha]_D^{25} = +20.00$ (cl.085, ethanol).

Elemental Analysis for C$_{18}$H$_{22}$KN$_5$O$_3$S: Calc'd: C, 50.56; H, 5.19; N, 16.38; Found: C, 50.20; H, 5.28; N, 16.02.

EXAMPLE 2

1-[[4-(1H-Tetrazol-5-yl-methyl)phenoxy]methyl]cyclohexane

A 1 L round bottom flask equipped with a magnetic stirrer, reflux condenser and nitrogen inlet was charged with 28.4 g anhydrous potassium carbonate (pulverized with mortar and pestle), cesium carbonate (catalytic amount), 4-(hydroxy)phenyl acetonitrile (18.26 g.), cyclohexylmethylbromide (36.4 g.) and dimethylformamide (600 mL). The mixture was heated to reflux and maintained for one week at this temperature under a nitrogen atmosphere. The reaction mixture was then cooled to room temperature and saturated aqueous NaCl and ethyl acetate were added. The layers were separated and the aqueous phase was extracted with ethyl acetate. The combined organic fractions were washed with saturated aqueous NaCl, dried over MgSO$_4$, filtered and concentrated in a rotary evaporator. The crude product was partitioned between equal volumes of hexane and 25% aqueous NaOH. This mixture was stirred under nitrogen atmosphere at room temperature for three days. The aqueous layer was drawn off, and the organic layer was washed with saturated aqueous NaCl, dried over MgSO$_4$, filtered and concentrated to give 23 g of 4-(cyclohexylmethoxy)-phenylacetonitrile as a yellow solid (73% yield). This material was homogeneous by TLC (CH$_2$Cl$_2$) and was carried on directly to the next step without further purification.

A mixture of 4-(cyclohexylmethoxy)phenylacetonitrile (15 g, prepared in the preceding paragraph), sodium azide (21.3 g), ammonium chloride (17.4 g) and dimethylformamide (325 mL) was heated to 135° C. under a nitrogen atmosphere for 40 hours. The mixture was then cooled to room temperature and enough water was added to dissolve all the salts. The homogeneous solution was then poured into a separatory funnel containing saturated aqueous NaCl and ethyl acetate. After extraction of the aqueous phase with additional ethyl acetate, the combined extracts were washed with saturated brine solution, dried over MgSO$_4$ and concentrated. The dark amber oil so obtained was treated with a little water and the resulting solid filtered off and crystallized from dichloromethane-diethyl ether mixture to afford 10.5 g (59% yield) of the title compound; m.p. 156°–158° C.

Elemental Analysis for C$_{15}$H$_{20}$N$_4$O: Calc'd: C, 66.15; H, 7.4; N, 20.57; Found: C, 65.86; H, 7.39; N, 20.24.

EXAMPLE 3

2-Methyl-2-[[4-(1H-tetrazol-5-yl-methyl)phenoxy]cyclohexanone

2-Hydroxymethyl-2-methylcyclohexanone [Pearson et al., J. Chem. Soc. Perkin I, 2774, 2778 (1980)] (3.7 g), 4-hydroxybenzyl cyanide (4.49 g) and triphenylphosphine (8.86 g) were dissolved in benzene (100 mL) and cooled in ice under a nitrogen atmosphere. Diethylazodicarboxylate (5.3 mL) was added dropwise and the mixture was allowed to warm to room temperature. The reaction was then refluxed overnight. After cooling to room temperature, the reaction mixture was diluted with 25% aqueous NaOH and extracted with benzene. The extracts were washed with saturated brine solution, dried over MgSO$_4$, filtered and concentrated. The crude residue was chromatographed on SiO$_2$, elution with dichloromethane to give 4.35 g (65% yield) of 2-methyl-2-[[4-(cyanomethyl)phenoxy]methyl]cyclohexanone as an amber oil.

A mixture of 2-methyl-2-[[4-(cyanomethyl)phenoxy]methyl]cyclohexanone (4.35 g, prepared in the preceding paragraph), sodium azide (5.5 g), ammonium chloride (4.48 g) and dimethylformamide (85 mL) was heated under a nitrogen atmosphere in an oil bath (controlled at 135° C.) for 15 hours. Enough water was added to the hot mixture to dissolve all suspended salts. The homogeneous solution was then transferred to a separatory funnel, diluted with saturated brine solution and extracted with ethyl acetate. The extracts were washed with saturated brine solution, dried over MgSO$_4$, filtered and concentrated. The crude product was chromatographed on silica gel (40 wt. eq.) by elution with a hexane-ethyl acetate-acetic acid gradient (70:30:2→5). The isolated amber oil solidified while under vacuum overnight. The solid was recrystallized from acetone-diethyl ether, yielding the title compound as while needles (1.45 g.); m.p. 118°-120° C.

Elemental Analysis for $C_{16}H_{20}N_4O_2$: Calc'd: C, 63.98; H, 6.71; N, 18.65; Found: C, 63.72; H, 6.60; N, 18.41.

EXAMPLE 4

1-Hydroxy-2-methyl-2-[[4-(1H-tetrazol-5-yl-methyl)-phenoxy]methyl]cyclohexane The title compound from Example 3, above, (0.54 g) was dissolved in dichloromethane (10 mL) and cooled in ice under a nitrogen atmosphere. Sodium borohydride (100 mg) in water (5 mL) was added dropwise to the keto tetrazole containing solution. The reaction mixture was allowed to warm to room temperature gradually and stirred overnight. The reaction mixture was cooled in ice and acidified to pH≦4 with dropwise addition of 10% HCl solution. The two phase mixture was then poured onto saturated brine solution and extracted with dichloromethane. The extracts were concentrated in a rotary evaporator, redissolved in ethanol (5 mL) and treated with NaOH (0.65 g). The homogeneous solution was allowed to stir at room temperature overnight. The solvent was removed in vacuo and the residue suspended between equal volumes of 10% HCl and ethyl acetate. The phases were separated and the aqueous phase was extracted with ethyl acetate. The combined organic phases were washed with saturated brine solution, dried over $MgSO_4$ and concentrated. The oily residue eventually hardened and crystals were obtained by scratching with a glass rod. The title compound so obtained is a mixture of isomers; m.p. 103°-108° C.

Elemental Analysis for $C_{16}H_{22}N_4O$: Calc'd: C, 63.56; H, 7.33; N, 18.53; Found: C, 63.39; H, 7.31; N, 18.25.

EXAMPLE 5

4,7,7-Trimethyl-3-oxo-N-[4-(1H-tetrazol-5-yl-methyl)-phenyl]-2-oxabicyclo[2.2.1]heptane-1-carboxamide A mixture of 4-aminobenzylnitrile (6.2 g), triethylamine (7 mL) and dichloromethane was cooled in ice under nitrogen. Camphanic acid chloride (10 g) in dichloromethane (50 mL) was added dropwise. The reaction mixture was allowed to warm to room temperature gradually overnight. The mixture was treated with 10% HCl solution (100 mL) for 2 hours, the phases were then separated and the organic phase was washed with 10% HCl and saturated brine solution. The product was dried over $MgSO_4$, filtered and concentrated to give 10.4 g of 4,7,7-trimethyl-3-oxo-N-[4-(cyanomethyl)-phenyl]-2-oxabicyclo[2.2.1]heptane-1-carboxamide as a dark yellow solid, homogeneous by TLC m.p. 147°-152° C.

4,7,7-Trimethyl-3-oxo-N-[4-(cyanomethyl)phenyl]-2-oxabicyclo[2.2.1]-heptane-1-carboxamide (6 g, prepared in the preceding paragraph), sodium azide (6.24 g), ammonium chloride (5.1 g) and dimethylformamide (100 mL) were heated in a 135° C. oil bath for 20 hours under a nitrogen atmosphere. Water was added to the hot mixture until homogeneity was achieved. The mixture was then cooled to room temperature, poured onto saturated brine solution in a separatory funnel, and extracted with ethyl acetate. The extracts were washed with saturated brine solution, dried over $MgSO_4$ and concentrated in a rotary evaporator. The crude product was dissolved in hot acetone, then cooled in a 0° C.

freezer to yield 4.1 g. (60% yield) of the title compound as a dark yellow solid; m.p. 224°-225° C. (dec.).

Elemental Analysis for $C_{18}H_{21}N_5O_3$: Calc'd: C, 60.75; H, 6.08; N, 19.68; Found: C, 60.53; H, 5.99; N, 19.42.

EXAMPLE 6

2-Methyl-2-[[4-(1H-tetrazol-5-yl-methyl)phenoxy]methyl]cyclohexanone oxime

2-Methyl-2-[[4-(1H-tetrazol-5-yl-methyl)phenoxy]-methyl]cyclohexanone (0.79 g, prepared in Example 3), hydroxylamine hydrochloride (0.22 g), sodium acetate (0.26 g) and ethanol (absolute, 20 ml) were combined and heated to reflux for 4 hours. The ethanol was removed in vacuo. The residue was partitioned between ethyl acetate and 10% HCl solution. The organic phase was washed with saturated aqueous NaCl solution, dried over $MgSO_4$ and concentrated on the rotary evaporator. The product was triturated with dichloromethane-diethyl ether mixture to afford 0.47 g of white solid, mp 153°-156° C. Analytical HPLC showed the product was 97.7% pure.

Elemental Analysis for $C_{16}H_{21}N_5O_2$: Calc'd: C, 60.94; H, 6.71; N, 22.21; Found: C, 61.12; H, 6.92; N, 21.65.

The antihyperglycemic activity of the compounds of this invention was established by subjecting them to the following standard experimental procedure for that purpose:

Eight to ten week old genetically obese (ob/ob) mice are randomly placed in groups of nine animals. Unless otherwise indicated in the following table, the compound being tested is administered in single oral doses for two consecutive days. The blood sample is taken on the third day at the normal dosing time. The concentration of glucose in plasma obtained from the blood samples is determined and reported as the mean±standard error for each test group of nine animals and compared to vehicle control and ciglitazone as the standard.

The results of these tests are as follows:

| Dose (mg/kg) | Glucose (mg/dl) | | |
|---|---|---|---|
| | Vehicle Control | Standard | Example |
| | | | (1) |
| 25 | 189 ± 7 | 116 ± 5 | |
| 75 | 189 ± 7 | | 115 ± 9 |
| 75 | 155 ± 11 | 96 ± 8 | |
| 5 | 155 ± 11 | 150 ± 9 | 121 ± 9 |
| 2 | 187 ± 15 | 142 ± 16 | 128 ± 8 |
| 5 | | 106 ± 11 | 162 ± 15* |
| 25 | | 105 ± 7 | 144 ± 11* |
| 75 | | 104 ± 5 | 160 ± 15* |
| 2 | 147 ± 20 | 117 ± 8 | 133 ± 13* |
| 5 | | 107 ± 7 | 140 ± 16* |
| 25 | | 125 ± 9* | 145 ± 11* |
| 75 | | 91 ± 4 | 109 ± 5 |
| | | | (1)[b] |
| 75 | 264 ± 33 | 102 ± 3 | 198 ± 17 (acid) |
| 75 | 264 ± 33 | 102 ± 3 | 188 ± 19 |
| | | | (2)[a] |
| 75 | −6 ± 12 | −44 ± 19 | |
| 300 | | | −45 ± 16 |
| 75 | 18 ± 26 | −64 ± 18 | 6 ± 17* |
| | | | (2)[b] |
| 75 | 264 ± 33 | 102 ± 3 | 218 ± 25* |
| 150 | 264 ± 33 | 99 ± 4 | |
| 150 | 264 ± 33 | 102 ± 33 | 160 ± 22 |
| 300 | 264 ± 33 | 102 ± 33 | 123 ± 111 |
| | | | (3)[b] |
| 75 | 208 ± 16 | 99 ± 5 | 131 ± 11 |

-continued

| Dose (mg/kg) | Glucose (mg/dl) | | |
|---|---|---|---|
| | Vehicle Control | Standard | Example |
| 5 | | 130 ± 12 | |
| | | | (4)[b] |
| 20 | 125 ± 8 | 93 ± 5 | 109 ± 3 |
| 75 | 264 ± 33 | 102 ± 3 | 124 ± 15 |
| | | | (5)[b] |
| 75 | 146 ± 9 | 89 ± 3 | 120 ± 8 |
| 75 | 264 ± 33 | 102 ± 3 | 176 ± 16 |
| | | | (6)[b] |
| 75 | 264 ± 33 | 102 ± 3 | 148 ± 13 |

*Not significantly different from control.
[a]Glucose values represent the mean change from day 1 to day 3.
[b]After 4 days of oral dosing, blood sample on 5th day.

From the experimental data obtained, it is apparent that the compounds of this invention reduce blood glucose levels, which characterizes them as antihyperglycemic agents useful in the treatment of disease states involving abnormally high blood levels of glucose, such as diabetes mellitus. As such, the compounds of this invention are to be administered to a mammal suffering from excessive blood levels of glucose in an amount from about 75 mg. to about 400 mg. per kilogram body weight, or more, per day, in single or multiple doses. An optimum dosing regimen to achieve the desired therapeutic response must be individualized for the patient by following the post-administration glucose blood levels. The dosage will vary with the compound administered and with the patient's age, weight, severity of disease state, response, etc., as is common in all therapeutic methods for control of glucose levels.

The compounds of this invention are orally active and may be made up in conventional unit dosage forms for administration. Compositions with inert diluents or edible carriers are compressed into tablets or filled in hard or soft gelatin capsules, with sufficient active ingredient to supply a daily dose or any fraction thereof. Slow release formulations are especially suitable for control of glucose with the compounds of this invention.

What is claimed is:

1. A compound of the formula:

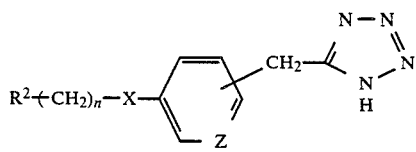

in which
R² is

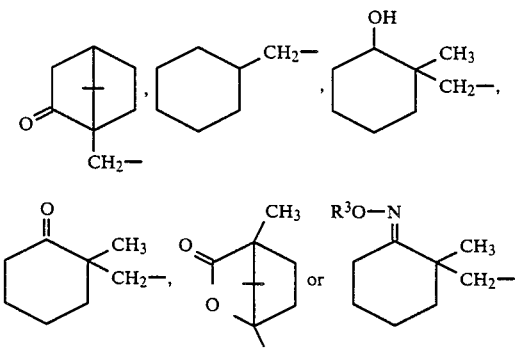

where
R³ is hydrogen, alkyl of 1 to 6 carbon atoms, or benzyl;
n is one of the integers 0, 1, 2 or 3;
X is —O—,

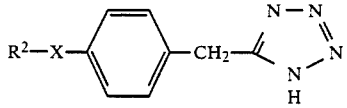

or —SO₂NH—;
and
Z is =CH— or —N=;
or a pharmaceutically acceptable salt thereof.

2. A compound of the formula:

in which
R² is

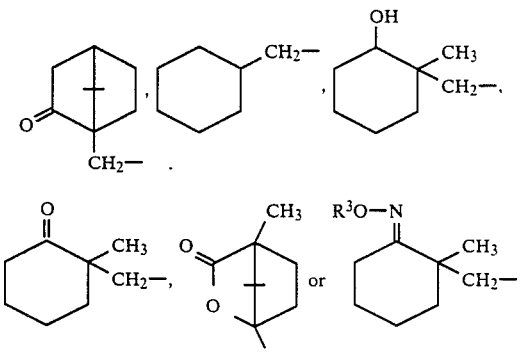

where
R³ is hydrogen, alkyl of 1 to 6 carbon atoms, or benzyl;
X is —O—, $$-\overset{O}{\underset{\|}{C}}NH-$$

or —SO₂NH—; or a pharmaceutically acceptable salt thereof.

3. A compound of claim 2 which is (+)-(7,7-dimethyl-2-oxo-N-[4-(1H-tetrazol-5-yl-methyl)phenyl]bicyclo[2.2.1]heptane)-1-methanesulfonamide, or a pharmaceutically acceptable salt thereof.

4. A compond of claim 2 which is 1-[[4-(1H-tetrazol-5-yl-methyl)phenoxy]methyl]cyclohexane, or a pharmaceutically acceptable salt thereof.

5. A compound of claim 2 which is 2-methyl-2-[[4-(1H-tetrazol-5-yl-methyl)phenoxy]methyl]cyclohexanone, or a pharmaceutically acceptable salt thereof.

6. A compound of claim 2 which is 1-hydroxy-2-methyl-2-[[4-(1H-tetrazol-5-yl-methyl)phenoxy]methyl]cyclohexane, or a pharmaceutically acceptable salt thereof.

7. A compound of claim 2 which is 4,7,7-trimethyl-3-oxo-N-[4-(1H-tetrazol-5-yl-methyl)phenyl]-2-oxabicyclo[2.2.1]heptane-1-carboxamide, or a pharmaceutically acceptable salt thereof.

8. A compound of claim 2 which is 2-methyl-2-[[4-(1H-tetrazol-5-yl-methyl)phenoxy]methyl]cyclohexanone oxime or a pharmaceutically acceptable salt thereof.

* * * * *